(12) United States Patent
Shen et al.

(10) Patent No.: US 8,282,957 B2
(45) Date of Patent: Oct. 9, 2012

(54) COATED PARTICLES CONTAINING PHARMACEUTICALLY ACTIVE AGENTS

(75) Inventors: Robert Shen, North Wales, PA (US); Vincent Chen, Dayton, NJ (US); Der-Yang Lee, Flemington, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 139 days.

(21) Appl. No.: 12/490,465

(22) Filed: Jun. 24, 2009

(65) Prior Publication Data

US 2009/0324716 A1 Dec. 31, 2009

Related U.S. Application Data

(60) Provisional application No. 61/075,767, filed on Jun. 26, 2008.

(51) Int. Cl.
*A61K 9/26* (2006.01)
(52) U.S. Cl. .................................. 424/469; 424/490
(58) Field of Classification Search ................. None
See application file for complete search history.

(56) References Cited

U.S. PATENT DOCUMENTS

| | | | |
|---|---|---|---|
| 3,185,626 A | 5/1965 | Baker | |
| 4,173,626 A | 11/1979 | Dempski et al. | |
| 4,543,370 A | 9/1985 | Porter et al. | |
| 4,643,894 A | 2/1987 | Porter et al. | |
| 4,683,256 A | 7/1987 | Porter et al. | |
| 4,725,441 A | 2/1988 | Porter et al. | |
| 4,802,924 A | 2/1989 | Woznicki et al. | |
| 4,828,841 A | 5/1989 | Porter et al. | |
| 4,851,226 A | 7/1989 | Julian et al. | |
| 4,863,742 A | 9/1989 | Panoz et al. | |
| 4,906,478 A | 3/1990 | Valentine et al. | |
| 4,980,170 A | 12/1990 | Schneider et al. | |
| 4,984,240 A | 1/1991 | Keren-Zvi et al. | |
| 5,075,114 A | 12/1991 | Roche | |
| 5,275,822 A | 1/1994 | Valentine et al. | |
| 5,286,497 A | 2/1994 | Hendrickson et al. | |
| 5,489,436 A | 2/1996 | Hoy et al. | |
| 5,630,871 A | 5/1997 | Jordan | |
| 5,658,589 A | 8/1997 | Parekh et al. | |
| 5,912,013 A | 6/1999 | Rudnic et al. | |
| 6,103,260 A | 8/2000 | Luber et al. | |
| 6,270,805 B1 | 8/2001 | Chen et al. | |
| 6,274,162 B1 | 8/2001 | Steffenino et al. | |
| 6,322,819 B1 | 11/2001 | Burnside et al. | |
| 6,767,200 B2 | 7/2004 | Sowden et al. | |
| 7,598,335 B2 | 10/2009 | Wang et al. | |
| 2004/0091538 A1 | 5/2004 | Pollock-Dove et al. | |
| 2004/0156902 A1 | 8/2004 | Lee et al. | |
| 2004/0241235 A1* | 12/2004 | Lebon et al. ................. | 424/471 |
| 2005/0112193 A1 | 5/2005 | Phillips et al. | |
| 2005/0152970 A1 | 7/2005 | Rinker et al. | |
| 2005/0214371 A1 | 9/2005 | DiCapua et al. | |
| 2008/0004470 A1 | 1/2008 | Mathad et al. | |
| 2008/0193522 A1 | 8/2008 | Meier et al. | |
| 2008/0206350 A1* | 8/2008 | Gryczke ....................... | 424/501 |
| 2008/0254112 A1* | 10/2008 | Klokkers et al. ............. | 424/456 |
| 2010/0086592 A1* | 4/2010 | Singh et al. .................. | 424/472 |
| 2010/0151010 A1* | 6/2010 | Petereit et al. ............... | 424/452 |

FOREIGN PATENT DOCUMENTS

| | | |
|---|---|---|
| CN | 101137354 A | 3/2008 |
| EP | 2098250 A | 9/2009 |
| WO | WO 2008/081891 A | 7/2008 |
| WO | WO 2009/037264 A | 3/2009 |

OTHER PUBLICATIONS

United States Pharmacopoeia (USP) No. 29 "Uniformity of Dosage Units", pp. 2778-2783, Jan. 2006.
Leiberman et al., "Pharmaceutical Dosage Forms, Tablets", vol. 2, 2nd ed., (1990) pp. 213-217 and pp. 327-329.
Lachman et al. "The Theory and Practice of Industrial Pharmacy", Chapter 11 3rd ed. (1986).

* cited by examiner

*Primary Examiner* — Bethany Barham
(74) *Attorney, Agent, or Firm* — William E. McGowan

(57) ABSTRACT

The present invention features a tablet including particles containing a pharmaceutically active agent, wherein the particles are coated with (a) a first film layer containing a modified release polymer; and (b) a second film layer containing (i) a first polymer, wherein the first polymer is a polymer of ethyl acrylate and methyl methacrylate and (ii) a second polymer, wherein the second polymer is a polymer of methyl acrylate, methyl methacrylate and methacrylic acid.

20 Claims, No Drawings

COATED PARTICLES CONTAINING PHARMACEUTICALLY ACTIVE AGENTS

CROSS REFERENCE TO RELATED APPLICATION

This application claims priority of the benefits of the filing of U.S. Provisional Application Ser. No. 61/075,767 filed Jun. 26, 2008.

BACKGROUND OF THE INVENTION

Compressed tablets (e.g., caplets) are known as one of the most cost effective, consumer friendly and convenient dosage forms available for delivering pharmaceutically active agents. Compressed tablets often involve multiple steps in order to incorporate pharmaceutically active agents into the form since only certain materials may be used for compression. The materials must have the correct compression characteristics such as flow and compressibility, in order to maintain operability on a tablet press, retain shape and form without breakage, and dissolve within an appropriate timeframe in the gastrointestinal tract. In order to achieve these characteristics, blends or powdered materials must often be granulated using high shear, chilsonation, or fluid bed techniques to increase the size and maintain a flowable particle shape. Methods for direct compression and wet granulation processes are known in the art, and are described in detail in, for example, Lachman, et al., *The Theory and Practice of Industrial Pharmacy*, Chapter 11 (3rd ed. 1986).

Compressed tablets have been used to deliver pharmaceutically active agents with a modified release profile. One means to make such tablets is to coat particles containing the pharmaceutically active agent with modified release polymers. However, these polymers often have the disadvantage of cracking under contact with the surrounding tablet matrix materials within the tablet upon compression. A cracked or ruptured coating may result in an pharmaceutically active agent, which no longer retains the intended modified release property. One means to overcome this issue was using a high level of plasticizers in the coating. However, plasticizers can also compromise the modified release properties of the polymer and/or lead to the portions of tablet sticking on the face of tablet tooling. When portions of the tablet stick, several issues may occur, including weight variation amongst individual tablets and removal of embossed markings. Another means to overcome these issues was the addition of high tensile strength polymers such as cellulose acetate to the coating. However, a disadvantage of this approach may include the use of solvents for applying the coating and/or the effect of the polymer in unfavorably changing the release properties of the coating.

The present invention provides for particles containing a pharmaceutically active agent that are coated with two film layers and that are compatible to be compressed in a tablet.

SUMMARY OF THE INVENTION

In one aspect, the present invention features a tablet including particles containing a pharmaceutically active agent, wherein the particles are coated with (a) a first film layer containing a modified release polymer and (b) a second film layer containing (i) a first polymer, wherein the first polymer is a polymer of ethyl acrylate and methyl methacrylate and (ii) a second polymer, wherein the second polymer is a polymer of methyl acrylate, methyl methacrylate, and methacrylic acid.

In another aspect, the present invention features a particle containing a pharmaceutically active agent, wherein the particles are coated with (a) a first film layer containing a modified release polymer and (b) a second film layer containing (i) a first polymer, wherein the first polymer is a polymer of ethyl acrylate and methyl methacrylate and (ii) a second polymer, wherein the second polymer is a polymer of methyl acrylate, methyl methacrylate, and methacrylic acid.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

Particles

The present invention features particles including a pharmaceutically active agent (e.g., one or more pharmaceutically active agents). In one embodiment, the particles are coated with (a) a first film layer including a modified release polymer and (b) a second film layer including (i) a first polymer, wherein the first polymer is a polymer of ethyl acrylate and methyl methacrylate and (ii) a second polymer, wherein the second polymer is a polymer of methyl acrylate, methyl methacrylate, and methacrylic acid.

First Film Layer

The first film layer includes a modified release polymer. As used herein, "modified release" shall apply to the altered release or dissolution of a pharmaceutically active agent in a dissolution medium, such as gastrointestinal fluids. Types of modified release include (i) extended release and (ii) delayed release. In general, modified release tablets are formulated to make the pharmaceutically active agent(s) available over an extended period of time after ingestion, which thereby allows for a reduction in dosing frequency compared to the dosing of the same pharmaceutically active agent(s) in a conventional tablet. Modified release tablets also permit the use of pharmaceutically active agent combinations wherein the duration of one pharmaceutically active agent may differ from the duration of another pharmaceutically active agent.

By "extended release," it is meant that, after administration, a pharmaceutically active agent is released from the tablet in a substantially continuous, regulated manner, and the time for complete release, e.g., depletion, of the pharmaceutically active agent from the tablet is longer than that associated with an immediate release tablet of the same. Types of extended release include controlled, sustained, and prolonged release, and may be zero-order or first-order release.

By "delayed release," it is meant that, after administration, there is at least one period of time when an pharmaceutically active agent is not being released from the tablet, e.g., the release of the pharmaceutically active agent(s) occurs at a time other than immediately following oral administration. Delayed release may include pulsatile release or pH dependent release, such as enteric release.

Solid dose formulations may employ polymers which display modified release characteristic forms in a variety of ways; including tablet coatings, tablet wet granulations, tablet direct compression in a tablet matrix, and particle coating. Examples of modified release polymers for use in particle coating include, but are not limited to, ethylcellulose, cellulose acetate, hydroxypropyl cellulose, hypromellose, polyvinyl acetate, polyvinyl alcohol and polymethacrylic acid polymers such as meth-/acrylates copolymers with trimethylammonioethylmethacrylate as a functional group commercially available from the Evonik Corporation (Theodore, Ala., USA) as Eudragit RS™ and Eudragit RL™.

Examples of suitable release modifying coatings for particles are described in U.S. Pat. Nos. 4,173,626; 4,863,742; 4,980,170; 4,984,240; 5,286,497; 5,912,013; 6,270,805; and 6,322,819.

Commercially available modified release pharmaceutically active agents may also be employed. For example, acetaminophen particles, which are encapsulated with release-modifying polymers by a coaccervation process, may be used in the present invention. Such coaccervation-encapsulated acetaminophen is commercially available from, for example, Eurand America, Inc. (Vidalia, Ohio, USA) or Circa Inc. (Dayton, Ohio, USA).

In one embodiment, the modified release polymer is a film-forming pH-dependent polymer, such as enteric polymers. Examples of a film-forming pH-dependent polymers include, but are not limited to, enteric cellulose derivatives, such as for example hydroxypropyl methylcellulose phthalate, hydroxypropyl methylcellulose acetate succinate, and cellulose acetate phthalate; natural resins, such as shellac and zein; enteric acetate derivatives such as for example polyvinylacetate phthalate, cellulose acetate phthalate, and acetaldehyde dimethylcellulose acetate; and enteric acrylate derivatives such as polymethacrylate-based polymers such as poly(methacrylic acid, methyl methacrylate) 1:2, which is commercially available under the tradename, EUDRAGIT S™, and poly(methacrylic acid, methyl methacrylate) 1:1, which is commercially available under the tradename, EUDRAGIT L™, and mixtures thereof.

The first film layer may contain a plasticizer in an amount of from about 0.01 percent to about 40 percent of the first coating, such as from about 1 percent to about 20 percent by weight of the first coating. Examples of suitable plasticizers for use in the first coating include glycerin, polyethylene glycol, propylene glycol, dibutyl sebecate, triethyl citrate, triacetin, tributyl citrate, vegetable oils such as castor oil, surfactants such as polysorbate-80, sodium lauryl sulfate and dioctyl-sodium sulfosuccinate, and polycarbohydrates. In one embodiment, the first film layer also contains pigments and/or opacifiers.

In one embodiment, the average thickness of the first film layer is from about 1 micron to about 20 microns, e.g. from about 2 microns to about 15 microns or from about 4 to about 9 microns. The first film layer may be present in an amount, based upon the total weight of the coated particle before the addition of the second coating thereto, from about 5 percent to about 60 percent, e.g. from about 25 percent to about 60 percent.

In one embodiment, the first film layer is from about 10 percent to about 60 percent by weight of the total weight of the particle after the addition of the second film layer, such as from about 15 percent to about 45 percent by weight of the total weight of the particle.

Second Film Layer

The second film layer includes (i) a first polymer, wherein the first polymer is a polymer of ethyl acrylate and methyl methacrylate and (ii) a second polymer, wherein the second polymer is a polymer of methyl acrylate, methyl methacrylate, and methacrylic acid.

Examples of first polymers include, but are not limited to, ethyl acrylate, methyl methacrylate copolymer 2:1 (commercially available as Eudragit NE-30D™ and Eudragit NE-40D™.

Examples of second polymers include, but are not limited to, methyl acrylate, methyl methacrylate and methacrylic acid 7:3:1 (commercially available as Eudragit FS-30D™).

In one embodiment, the weight ratio of the first polymer to the second polymer is from about 1:3 to about 3:1, such as from about 1.5:1 to about 2.5:1.

In one embodiment, the second film layer includes from about 25 percent to about 75 percent, by weight, of the first polymer and from about 75 percent to about 25 percent, by weight, of the second polymer; such as from about 60 percent to about 75 percent, by weight, of the first polymer and from about 25 percent to about 40 percent, by weight, of the second polymer In one embodiment, the second film layer is from about 20 percent to about 50 percent, such as about 25 percent to about 45 percent by weight of the total weight of the particles including the first and the second coating layers The second coating layer may contain additional materials such as, for example, anti-tack agents or surfactants. Suitable anti-tack agents may include, but are not limited to, talc and magnesium stearate. Examples of suitable surfactants include both ionic and non-ionic materials from both synthetic and natural origins, including but not limited to lecithin, glyceryl esters, sugar esters, polysorbates, mono and diglycerides of fatty acids, propylene glycol esters, sucrose fatty acid esters, polyoxyethylene derivatives of sorbitan fatty acid esters, and simethicone. Examples of useful polysorbates include sorbitan trioleate, sorbitan monopalmitate, sorbitan monolaurate, propylene glycol monolaurate, glycerol monostearate, diglycerol monostearate, and glycerol lactyl-palmitate. Lactic acid derivatives include, but are not limited to, sodium stearoyl lactylate and calcium stearoyl lactylate. In one embodiment when a surfactant is present in the second coating layer, the level of surfactant is present in an amount, based upon the total weight of the second coating layer, of from about 0.5 percent to about 10 percent. In one embodiment, magnesium stearate is used at a level of about 2 percent to about 20 percent by weight of the second coating.

In one embodiment, the average thickness of the second coating layer on the coated core is from about 1 to about 20 microns, e.g., from about 2 to about 15 microns or from about 4 microns to about 9 microns.

Manufacture of Pharmaceutically Active Agent Containing Particles

In one embodiment, the pharmaceutically active agent particle is directly coated with the first film layer, and is in the form of a crystal. In another embodiment, the pharmaceutically active agent is first layered on top of a substrate; either with or without the use of a binder and dried. The first and second layers of coating are then subsequently applied to the layered particles. Suitable substrates for layering include, but are not limited to, sugars and sugar alcohols (such as but not limited to dextrose monohydrate, sucrose, lactose, lactitol, sorbitol, mannitol, maltitol, xylitol, non pareil beads, and erythritol), starches (such as modified starches), and celluloses (such as microcrystalline cellulose). Suitable binders include but are not limited to hypromellose, hydroxypropyl cellulose, starch, modified starch, and polyvinylpyrrolidone.

In one embodiment, binders are incorporated in the layered particle from about 0.1 percent to about 10 percent by weight of the layered particle.

Pharmaceutically active agent layering may achieved by means of fluid bed layering, wherein the active is suspended or dissolved in a suitable solvent such as alcohol, water, propylene glycol, glycerin, acetone, isopropanol, and methanol, and subsequently sprayed onto the inert layer. Suitable fluid bed layering techniques include bottom spray, tangential spray and top spray layering; wherein the air flow, air temperature, spray rate and spray atomization are modified to optimize the particle size during layering. In one embodiment a lower dose pharmaceutically active agent is layered onto a higher dose pharmaceutically active agent. In one embodiment a binder is placed into the coating dispersion to facilitate binding to the inert layer. In one embodiment the binder is placed and blended into the fluidized powder with the inert material. In one embodiment the lower dose pharmaceutically active agent is loperamide, phenylephrine, pseudoephedrine, diphenhydramine, or chlorpheniramine and the higher dose pharmaceutically active agent is acetaminophen or ibuprofen. Suitable ratios of inert material to pharmaceutically active agent include, but are not limited to, from about 50:50 to about 99.5:0.5.

In one embodiment, the pharmaceutically active agent particles are granulated with another material such as a binder. This may be achieved by means including, but not limited to, wet granulation, high shear granulation, chilsonation, and fluid bed granulation. Suitable binders include those listed above. In another embodiment, more than one pharmaceutically active agents are co-granulated together prior to the addition of the modified release coatings. In one granulation embodiment, the pharmaceutically active agent is mixed with a filler and a binder, and wetted with water, alcohol or combination thereof, dried and optionally sized through a screen. In one embodiment the binder is made into a solution prior to addition to the pharmaceutically active agent.

Coating of Pharmaceutically Active Agent Containing Particles

The coatings which are applied to the pharmaceutically active agent particles can be layered on utilizing fluid bed coating wherein each layer is prepared in an aqueous (water based) or organic solvent system and sprayed in succession onto the fluidized bed of particles until the desired coating level is achieved. In an aqueous system, these polymers are generally prepared as a dispersion.

In one embodiment, the mean particle size of the coated particles can be from about 150 microns to about 320 microns, e.g. from about 220 to about 300 microns, following the granulation or layering step. In one embodiment, the mean particle size of the coated particle can be from about 200 to about 425 microns, e.g. from about 250 to about 375 microns following the addition of the first film coating layer. In one embodiment the mean particle size of the coated pharmaceutically active agent particle can be from about 300 microns to about 600 microns, e.g. from about 350 microns to about 525 microns, following the addition of the second film coating layer.

Use of Particles

In one embodiment, the coated particles are included in compressed tablets (e.g., for oral ingestion). In one embodiment, upon ingestion, the tablet is adapted to release from about 20 to about 50 percent (such as from about 25 to about 40 percent) of the pharmaceutically active agent contained within the coated particles within 2 hours of ingestion; from about 40 to about 70 percent (such as from about 50 to about 65 percent) of the pharmaceutically active agent within 4 hours of ingestion, and from about 65 to about 90 percent (such as from about 70 to about 80 percent) of the pharmaceutically active agent within 6 hours of ingestion. In another embodiment, the coated particles may be combined with an additional second pharmaceutically active agent within the tablet matrix. In one embodiment, the release rate of the first pharmaceutically active agent is substantially matched with the release rate of the second pharmaceutically active agent in the tablet matrix. In another embodiment, the release rate of the first pharmaceutically active agent in the particles is controlled such that the release rate of the first pharmaceutically active agent is matched with the clinical duration of the second immediate release pharmaceutically active agent in the tablet matrix. In one embodiment, the first pharmaceutically active agent is phenylephrine and the second pharmaceutically active agent, which is released immediately but which has a duration of at least 12 hours, is cetirizine. In one embodiment, the first pharmaceutically active agent is phenylephrine and the second pharmaceutically active agent, which is released immediately but which has a duration of at least 4 hours, is ibuprofen. In one embodiment, the first pharmaceutically active agent is phenylephrine and the second pharmaceutically active agent, which is released immediately but which has a duration of at least 6 hours, is naproxen.

As used herein, "substantially coated" shall mean that less than about 20 percent, e.g. less than about 15 percent, or less than about 1 percent of the surface area of a particle is exposed (e.g. not covered, with a desired coating).

Manufacture of Tablet

In one embodiment of the invention, the coated particles are mixed with a powder containing a pharmaceutically-acceptable carrier, which is also defined herein as the tablet matrix. In one embodiment, the powder has an average particle size of about 50 microns to about 500 microns, such as between 50 microns and 300 microns. Particles in this size range are particularly useful for direct compression processes.

In embodiment, the components of powder are blended together, for example as dry powders, and fed into the die cavity of an apparatus that applies pressure to form a tablet. Any suitable compacting apparatus may be used, including, but not limited to, conventional unitary or rotary tablet press. In one embodiment, the tablet may be formed by compaction using a rotary tablet press (e.g., such as those commercially available from Fette America Inc., Rockaway, N.J., or Manesty Machines LTD, Liverpool, UK). In general, a metered volume of powder is filled into a die cavity, where the powder is either gravity fed or mechanically fed from a feeder, of the rotary tablet press, and the cavity rotates as part of a "die table" from the filling position to a compaction position. At the compaction position, the powder is compacted between an upper and a lower punch, then the resulting tablet is pushed from the die cavity by the lower punch and then guided to an injection chute by a stationary "take-off" bar. Advantageously, when utilized, a direct compression process may enable the minimization or elimination of water-soluble, non-saccharide polymeric binders such as polyvinyl pyrrolidone, alginates, hydroxypropyl cellulose, and hydroxypropylmethylcellulose, hydroxyethylcellulose, which could have a negative effect on dissolution.

In another embodiment, the tablet may be prepared by the compression methods and apparatus described in United States Patent Application Publication No. 20040156902. Specifically, the tablet may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder recovery system to recover excess powder from the filters and return the powder to the dies.

In another embodiment, the tablet matrix may be prepared by a wet-granulation method, in which the excipients and a solution or dispersion of a wet binder (e.g., an aqueous cooked starch paste or solution of polyvinyl pyrrolidone) are mixed and granulated. Suitable apparatus for wet granulation include low shear mixers (e.g., planetary mixers), high shear mixers, and fluid beds (including rotary fluid beds). The resulting granulated material may then be dried, and optionally dry-blended with further ingredients (e.g., excipients such as lubricants, colorants, and the like). The final dry blend is then suitable for compression by the methods described in the previous paragraph. Methods for direct compression and wet granulation processes are known in the art. In one embodiment the tablet matrix includes a wet granulation, which is formulated to have modified release properties. In one embodiment, a lower dose pharmaceutically active agent is coated with coating of the present invention and mixed with a controlled release tablet matrix of a higher dose pharmaceutically active agent, and compressed into a tablet.

In one embodiment, the tablet is prepared by the compression methods and apparatus described in issued U.S. Pat. No. 6,767,200, the disclosure of which is incorporated herein by reference. Specifically, the tablet is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

In one embodiment of the invention, the tablet may be a directly compressed tablet made from a powder that is substantially free of water-soluble polymeric binders and hydrated polymers. As used herein, what is meant by "substantially free" is less than 5 percent, such as less than 1 percent, such as less than 0.1 percent, such as completely free (e.g., 0 percent). This composition is advantageous for maintaining an immediate release dissolution profile, minimizing processing and material costs, and providing for optimal physical and chemical stability of the tablet. In one embodiment the density of the tablet is greater than about 0.9 g/cc.

The tablet may have one of a variety of different shapes. For example, the tablet may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet has one or more major faces. For example, the tablet surface typically has opposing upper and lower faces formed by contact with the upper and lower punch faces in the compression machine. In such embodiments the tablet surface typically further includes a "belly-band" located between the upper and lower faces, and formed by contact with the die walls in the compression machine. A tablet may also be a multilayer tablet.

Alternatively, if tablets of the same composition are to be used in the dosage forms, the compression module may be equipped with multi-tip compression tooling. Four-tip tooling, for example, may be used to make four tablets within one die. The tablets may contain a single layer of multiple layers.

In certain embodiments, multilayer tablets can be produced with the invention described herein (e.g., bi-layer or tri-layer tablets can be produced). In one embodiment, the tablet die is filled with a first portion of the powder, the powder bed is optionally compressed a first time, a second portion of the powder is added, the tablet is compressed, and the tablet is ejected from the die. In one embodiment, the second portion of powder has the same blend composition as the first portion of powder. In another embodiment, the second portion of powder has a different composition from the first portion of powder. In one embodiment the first portion of the powder contains a pharmaceutically active agent and the second portion of the powder contains a different pharmaceutically active agent. In one embodiment, the first portion is for immediate release and the second portion is for modified release. In one embodiment the first portion contains an immediate release dose of the first and second pharmaceutically active agents, and the second portion contains a portion of the first pharmaceutically active agent coated with the coatings of the present invention and a modified release tablet matrix containing the second pharmaceutically active agent.

One of the benefits of the coating composition of the present invention may be demonstrated via content uniformity analysis in accordance with the guidelines outlined in United States Pharmacopoeia (USP) No. 29. In particular, the content uniformity for a particular pharmaceutically active agent may be determined by measuring the concentration of pharmaceutically active agent in a random sampling of 10 tablets within a batch in order to determine if the samples have an overall relative standard deviation (RSD) of less than 6 percent, i.e., less than about 5 percent, or less than about 3 percent, or less than 2 percent, or less than about 1 percent. This would indicate that there would be little to no loss or sticking of tablet material to the tablet punch surfaces during the compression process.

An additional benefit of the coating composition of the present invention may be demonstrated via standard deviation analysis of the individual vessels in a dissolution. In particular, the standard deviation for a particular pharmaceutically active agent may be determined by measuring the concentration of pharmaceutically active agent in a dissolution vessel, when compared using the average of 6 vessels. In one embodiment, the standard deviation of 6 vessels is less than 6 percent, or less than 5 percent at any individual time point. This would indicate that there is a uniform level of cracking of the coating layers during the compression process, since the release rate would be uniform, further indicating that the second layer acted in performing a protective function.

Powder

As discussed above, the tablet is manufactured by compressing a powder containing a pharmaceutically-acceptable carrier. The carrier may contain one or more suitable excipients for the formulation of tablets. Examples of suitable excipients include, but are not limited to, fillers, adsorbents, binders, disintegrants, lubricants, glidants, release-modifying excipients, sweeteners, superdisintegrants, flavor and aroma agents, antioxidants, texture enhancers, and mixtures thereof.

Suitable fillers include, but are not limited to, water-soluble compressible carbohydrates such as sugars (e.g., dextrose, sucrose, maltose, and lactose), starches (e.g., corn starch), sugar-alcohols (e.g., mannitol, sorbitol, maltitol, erythritol, and xylitol), starch hydrolysates (e.g., dextrins, and maltodextrins), and water insoluble plastically deforming materials (e.g., microcrystalline cellulose or other cellulosic derivatives), and mixtures thereof.

Suitable adsorbents (e.g., to adsorb the liquid drug composition) include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN™ brand (Fuji Chemical Industries (USA) Inc., Robbinsville, N.J.), clays, silicas, bentonite, zeolites, magnesium silicates, hydrotalcite, veegum, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Suitable release-modifying excipients include, but are not limited to, swellable erodible hydrophilic materials, insoluble edible materials, pH-dependent polymers, and mixtures thereof.

Suitable swellable erodible hydrophilic materials for use as release-modifying excipients include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly (ethylene oxide). Examples of suitable acrylic polymers include, but are not limited to, potassium methacrylatedivinylbenzene copolymer, polymethylmethacrylate, high-molecular weight cross-linked acrylic acid homopolymers and copolymers commercially available from Noveon Chemicals under the tradename CARBOPOL™ (e.g., having a viscosity of greater than 50,000 centipoise when tested using a Brookfield RVT Viscometer at 25° C., using spindle #7, when dispersed in a basic solution). Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and tri-glycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, stearoyl macrogol-32 glycerides, and mixtures thereof Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof.

Suitable pH-dependent polymers for use as release-modifying excipients include, but are not limited to, enteric cellulose derivatives such as hydroxypropyl methylcellulose phthalate, hydroxypropyl methylcellulose acetate succinate, cellulose acetate phthalate; natural resins such as shellac and zein; enteric acetate derivatives such as polyvinylacetate phthalate, cellulose acetate phthalate, acetaldehyde dimethylcellulose acetate; and enteric acrylate derivatives such as polymethacrylate-based polymers such as poly(methacrylic acid, methyl methacrylate) 1:2 (which is commercially under the tradename EUDRAGIT S™), and poly(methacrylic acid, methyl methacrylate) 1:1 (which is commercially available under the tradename EUDRAGIT L™), and mixtures thereof.

Examples of suitable sweeteners include, but are not limited to, synthetic or natural sugars, sucralose, saccharin, sodium saccharin, aspartame, acesulfame K or acesulfame, potassium acesulfame, thaumatin, glycyrrhizin, dihydrochalcone, alitame, miraculin, monellin, stevside, and mixtures thereof.

Examples of superdisintegrants include, but are not limited to, croscarmellose sodium, sodium starch glycolate and cross-linked povidone (crospovidone). In one embodiment the tablet contains up to about 5 percent by weight of such superdisintegrant.

Examples of suitable flavor and aroma agents include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry, and black currant); artificial and natural flavors of brews and liquors (e.g., cognac, whisky, rum, gin, sherry, port, and wine); tobacco, coffee, tea, cocoa, and mint; fruit juices including expelled juice from washed, scrubbed fruits such as lemon, orange, and lime; mint; ginger; cinnamon; cacoe/cocoa; vanilla; liquorice; menthol; eucalyptus; aniseeds nuts (e.g., peanuts, coconuts, hazelnuts, chestnuts, walnuts, and colanuts); almonds; raisins; and powder, flour, or vegetable material parts including tobacco plant parts (e.g., the genus *Nicotiana* in amounts not contributing significantly to a level of therapeutic nicotine), and mixtures thereof.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1 percent to about 10 percent by weight.

Pharmaceutically Active Agent

The tablet of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenhydroamine, dimenhydrinate, meclizine, promethazine, and hydroxyzine; probiotic bacteria including but not limited to lactobacilli; lactase; racecadotril; and anti-flatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, and orphenadrine, methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem; isomers thereof; and pharmaceutically acceptable salts and prodrugs thereof.

Examples of appetite suppressants include, but are not limited to, phenylpropanolamine, phentermine, and diethylcathinone; isomers thereof; and pharmaceutically acceptable salts and prodrugs thereof Examples of anesthetics (e.g., for the treatment of sore throat) include, but are not limited to dyclonene, benzocaine, and pectin; isomers thereof; and pharmaceutically acceptable salts and prodrugs thereof.

Examples of suitable statins include but are not limited to atorvastin, rosuvastatin, fluvastatin, lovastatin, simvustatin, atorvastatin, and pravastatin; isomers thereof; and pharmaceutically acceptable salts and prodrugs thereof.

In one embodiment, the pharmaceutically active agent included within the tablets selected from phenylephrine, dextromethorphan, pseudoephedrine, acetaminophen, ibuprofen, ketoprofen, loperamide, famotidine, calcium carbonate, simethicone, and menthol; isomers thereof; and pharmaceutically acceptable salts and prodrugs thereof.

In one embodiment, the pharmaceutically active agent is selected from phenylephrine, dextromethorphan, pseudoephedrine, chlorpheniramine, methocarbomal, chlophedianol, ascorbic acid, menthol, pectin, dyclonine, and benzocaine; isomers thereof; and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the granule prior to coating, or may be in the form of particles, which in turn may be coated. A second pharmaceutically active agent may be present in the coated particle, or uncoated in the tablet matrix. If the pharmaceutically active agent is in form of particles, the particles prior to coating, granulation, or layering typically have an average particle size of from about 1 to about 1000 microns. In one embodiment, such particles are crystals prior to coating, layering of granulation having an average particle size of from about 1 to about 300 microns. In another embodiment, the particles have an average particle size of from about 50 to about 2000 microns, such as from about 50 to about 1000 microns, such as from about 100 to about 800 microns.

If the second pharmaceutically active agent, which is not coated with the modified release coating of the present invention, has an objectionable taste, the second pharmaceutically active agent may be coated with a taste masking coating, as known in the art. Examples of suitable taste masking coatings are described in U.S. Pat. Nos. 4,851,226, 5,075,114, and 5,489,436. Commercially available taste masked pharmaceutically active agents may also be employed. For example, acetaminophen particles, which are encapsulated with ethylcellulose or other polymers by a coaccervation process, may be used in the present invention. Coaccervation-encapsulated acetaminophen may be purchased commercially from Eurand America, Inc. (Vandalia, Ohio) or from Circa Inc. (Dayton, Ohio).

The pharmaceutically active agent may be present in pure crystal form or in a granulated form prior to the addition of the modified release coating. Granulation techniques may be used to improve the flow characteristics or particle size of the pharmaceutically active agents to make it more suitable for compression or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation, the details of which are disclosed in, "The Theory and Practice of Industrial Pharmacy, $3^{rd}$ edition", Chapter 11, Lachman, Leon et al., 1986.

In one embodiment one or more pharmaceutically active agents or a portion of the pharmaceutically active agents may be bound to an ion exchange resin prior to the addition of the first coating of the present invention.

In one embodiment, the pharmaceutically active agent is capable of dissolution upon contact with a fluid such as water, stomach acid, intestinal fluid or the like In another embodiment, the dissolution characteristics of the pharmaceutically active agent are modified: e.g. controlled, sustained, extended, retarded, prolonged, delayed and the like when analyzed using USP dissolution apparatus 1 (baskets) and USP apparatus 2 (paddles) at 50 -150 rpm in the appropriate media including but not limited to water, 0.1N HCL, pH 5.8 phosphate buffer, and pH 7.2 phosphate buffer.

Tablets Coatings

In one embodiment, the method of the present invention furthers includes coating the tablet (e.g., with an outer coating). In one embodiment, the method further includes coating the tablet with a subcoating prior to applying the outercoating to the tablet.

Subcoating

In one embodiment, the tablet contains one or more subcoating layers. In one embodiment, the subcoating layer substantially covers the surface of the tablet. The use of subcoatings is well known in the art and disclosed in, for example, U.S. Pat. No. 3,185,626, which is incorporated by reference herein. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Suitable subcoatings may include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates; pigments; and opacifiers.

In one embodiment, the subcoating includes, based upon the total weight of the subcoating, from about 2 percent to about 8 percent (such as from about 4 percent to about 6 percent of a water-soluble cellulose ether and from about 0.1 percent to about 1 percent castor oil), as disclosed in detail in U.S. Pat. No. 5,658,589, which is incorporated by reference herein. In another embodiment, the subcoating includes, based upon the total weight of the subcoating, from about 20 percent to about 50 percent (such as from about 25 percent to about 40 percent) of HPMC; from about 45 percent to about 75 percent (such as from about 50 percent to about 70 percent) of maltodextrin; and from about 1 percent to about 10 percent (such as from about 5 percent to about 10 percent) of PEG 400.

The subcoating typically is present in an amount, based upon the dry weight of the tablet, from about 0 percent to about 5 percent. The dried dip coating layer typically is present in an amount, based upon the dry weight of the tablet and the optional subcoating, from about 1.5 percent to about 10 percent. In one embodiment the tablet is substantially free of a subcoating.

Outer-coating

What is meant by outer-coating is the coating on the outer surface of the coated tablet. In one embodiment, the outer-coating substantially covers (e.g., covers at least 90 percent) the surface of the tablet.

The average thickness of the dried dip-coating layer typically is from about 40 to about 400 microns. However, one skilled in the art would readily appreciate without undue experimentation that the dip coating thickness may be varied in order to provide a smoother, easier to swallow, tablet or to achieve a desired dissolution profile. Moreover, the thickness of dipped film coatings may vary at different locations on the substrate depending upon its shape. For example, the thickness of the coating at an edge or corner of a substrate may be as much as 50 percent to 70 percent less than the thickness of the coating at the center of a major face of the substrate. This difference can be minimized by, for example, use of a thicker subcoating, or use of dipping compositions that result in higher weight gains on the substrate.

In embodiments wherein a thicker dip coating is desired, an effective amount of a weight gain enhancer (e.g., simethicone, polysorbate 80 and mixtures thereof) may be added to a film forming composition containing a film former and an optional thickener such as a hydrocolloid. The weight gain enhancer is used in an amount sufficient to increase the weight gain of the coating liquid, e.g. by at least about 10 percent, by at least about 20 percent, or by at least about 30 percent on a substrate when dried. The percent weight gain increase is determined based upon the difference between the total weight of the coated substrate with the coating composition including the weight gain enhancer, and the total weight of an coated equivalent substrate, which has been coated under similar processing conditions with a coating composition that does not include an effective amount of weight gain enhancer.

In one embodiment, the method further includes creating one or more openings in the subcoating in the portion of the tablet that is not coated with the outer-coating, to expose the tablet on the surface of the coated tablet, such as described in US Patent Application No. 2005/0152970.

In one embodiment, the method further includes creating one or more openings in the outer-coating to expose the tablet, not through the subcoating, as disclosed in US Patent Application No. 2005/0152970. Since gelatin is not compatible with laser drilling, it is necessary in tablets with such gelatin coating, to expose the subcoat before laser drilling the openings.

In one embodiment the outer-coating covers only a portion of the tablet such as only one half of the coated tablet. The other half of the tablet may contain a separate type of the outer-coating such as gelatin, or expose only the subcoat or tablet.

In certain embodiments in which modified release of the pharmaceutically active agent is desired, the pharmaceutically active agent or the compressed tablet may optionally be coated with a known release-modifying coating. This advantageously provides an additional tool (e.g., in addition to the modified release coating on the particles) for modifying the release profile of pharmaceutically active agent from the tablet. In one embodiment, the coating contains a film-forming pH-dependent polymer, such as enteric polymers. In one embodiment, the outer coating is a modified release coating and the active coated particles in the tablet have a different modified release, so that variable release rates can be demonstrated; including a pulsatile release demonstrated by the tablet coating and a first order release demonstrated by the coated pharmaceutically active agent. In another embodiment, the outer modified release coating is placed on the tablet to release the a second uncoated pharmaceutically active agent particle from the tablet in a modified release manner, and the first particle coated pharmaceutically active agent in a separate modified release manner.

As used herein, "substantially coated" shall mean that less than about 20 percent, e.g. less than about 15 percent, or less than about 1.0 percent of the surface area of a tablet is exposed, e.g. not covered, with a desired coating.

In one embodiment, the tablet coating contains a thermoplastic film-forming water soluble polymer, such as a hydroxypropylmethylcellulose compound. An example of such a compound is "HPMC 291", which is a cellulose ether having a degree of substitution of about 1.9 and a hydroxypropyl molar substitution of 0.23, and containing, based upon the total weight of the compound, from about 29 percent to about 30 percent methoxyl groups and from about 7 percent to about 12 percent hydroxylpropyl groups. HPMC 2910 is commercially available from the Dow Chemical Company under the tradename METHOCEL E™. METHOCEL E5™, which is one grade of HPMC-2910 suitable for use in the present invention, has a viscosity of about 4 to 6 cps (4 to 6 milipascal-seconds) at 20 C in a 2 percent aqueous solution as determined by a Ubbelohde viscometer. Similarly, METHOCEL E6™, which is another grade of HPMC-2910 suitable for use in the present invention, has a viscosity of about 5 to 7 cps (5 to 7 milipascal-seconds) at 20 C in a 2 percent aqueous solution as determined by a Ubbelohde viscometer. METHOCEL E15™, which is another grade of HPMC-2910 suitable for use in the present invention, has a viscosity of about 15000 cps (15 milipascal-seconds) at 20 C in a 2 percent aqueous solution as determined by a Ubbelohde viscometer. As used herein, "degree of substitution" means the average number of substituent groups attached to an anhydroglucose ring, and "hydroxypropyl molar substitution" means the number of moles of hydroxypropyl per mole anhydroglucose.

In one embodiment, the coating contains a polyvinyl alcohol and polyethylene glycol copolymer. One suitable polyvinyl alcohol and polyethylene glycol copolymer for use as a tablet coating is commercially available from BASF Corporation under the tradename KOLLICOAT IR™.

In one embodiment, the coating contains a modified starch. As used herein, "modified starches" for use in the tablet coating include starches that have been modified by crosslinking, chemically modified for improved stability or optimized performance, or physically modified for improved solubility properties or optimized performance. Examples of chemically-modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to modified starches that have been pre-wetted, then dried to enhance their cold-water solubility.

Suitable modified starches for use in the tablet coating are commercially available from several suppliers such as, for example, A. E. Staley Manufacturing Company, and National Starch & Chemical Company. One suitable film forming modified starch includes the pre-gelatinized waxy maize derivative starches that are commercially available from National Starch & Chemical Company under the tradenames PURITY GUM™ and FILMSET™, and mixtures thereof Such waxy maize starches typically contain, based upon the total weight of the starch, from about 0 percent to about 18 percent of amylose and from about 100 percent to about 88 percent of amylopectin.

Other suitable film forming modified starches for use in the tablet coating include the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, PURE-COTE B790™.

In one embodiment, the tablet coating contains a tapioca dextrin. Suitable tapioca dextrins for use as film formers as tablet coatings include, but are not limited to, those available from National Starch & Chemical Company under the tradenames CRYSTAL GUM™ or K-4484™, and derivatives thereof such as modified food starch derived from tapioca, which is available from National Starch and Chemical under the tradename PURITY GUM 40™, and copolymers and mixtures thereof.

In one embodiment, the tablet coating contains a thickener. Examples of such thickeners include but are not limited to hydrocolloids (also referred to herein as gelling polymers), clays, gelling starches, and crystallizable carbohydrates, and mixtures thereof.

Examples of suitable hydrocolloids (also referred to herein as gelling polymers) for use as a tablet coating include alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and mixtures thereof. Examples of suitable gelling starches include acid hydrolyzed starches, and mixtures thereof. Additional suitable thickening hydrocolloids include low-moisture polymer solutions such as mixtures of gelatin and other hydrocolloids at water contents up to about 30 percent, such as for example those used to make "gummi" confection forms. Additional suitable thickeners include, but are not limited to, crystallizable carbohydrates.

In one embodiment of the invention, the tablet coating contains gelatin. Gelatin is a natural, thermogelling polymer. It is a tasteless and colorless mixture of derived proteins of the albuminous class, which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67 percent gelatin gel that has been held at 10 C for 17 hours. In a preferred embodiment, the flowable material is an aqueous solution including 20 percent 275 Bloom pork skin gelatin, 20 percent 250 Bloom Bone Gelatin, and approximately 60 percent water.

Use of Tablet

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlophedianol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

The tablet may be compressed at forces, which may rupture the outer particle coating, but not compromise the modified release properties displayed by the inner coating. As measure of the effectiveness of the two coatings, the tablet can be compressed at a certain compression force and display a certain hardness. Suitable compression forces are form about 2 kiloNewtons to about 30 kiloNewtons (e.g. from about 5 kiloNewtons to about 20 kiloNewtons). In one embodiment, the compressed tablet including the dual coated particles of the present invention has a hardness of more than about 5 kp/cm², such as more than 6 kp/cm², such as more than 9 kp/cm².

Hardness Test

In one embodiment, the tablet of the present invention has a mean hardness value of at least 5 kp/cm². Hardness is a term used in the art to describe the diametral breaking strength as measured by a Schleuniger Hardness Tester as described in Leiberman et al., Pharmaceutical Dosage Forms—Tablets, Volume 2, 2nd ed., Marcel Dekker Inc., 1990, pp. 213-217, 327-329. In order to perform the hardness test, a single tablet is placed into the steel chamber within the hardness tester, and the steel piston pushes against the dosage form until it breaks, measuring the force applied as a hardness measurement. In general, 5 tablets are tested from any one sample in order to provide a mean hardness value in kiloponds.

EXAMPLES

Specific embodiments of the present invention are illustrated by way of the following examples. This invention is not confined to the specific limitations set forth in these examples.

Example 1

Preparation of Modified Release Coating and Compression Protective Coating

A Modified Release Coating was prepared by dispersing, anionic copolymer of methacrylic acid and methacrylates (Eudragit RS-PO™), magnesium stearate, and acetyltributylcitrate in acetone/isopropyl alcohol (2 to 1) under ambient conditions, so that the finished dispersion contained 18 percent of the coating materials. The weight percentage of coating materials in the final film were, based upon the dried weight of final coating, is set forth in Table A below:

TABLE A

Composition of Modified Release Coating

| Component Name | Amount Present (wt. percent based on dried coating) |
|---|---|
| Eudragit RS PO | 62.5 percent |
| AcetylTributylCitrate (ATBC) | 15.6 percent |
| Magnesium Stearate | 21.9 percent |

In a separate container, a Compression Protective Coating was prepared by dispersing, Eudragit NE30D™ (a 30 percent aqueous suspension of ethyl acrylate, methyl methacrylate copolymer 2:1), Eudragit FS30D™ (a 30 percent aqueous dispersion of methyl acrylate, methyl methacrylate and methacrylic acid), magnesium stearate, simethicone, and sodium lauryl sulfate in purified water under ambient conditions, so that the finished dispersion contained 20.5 percent of the coating materials. The weight percentage of coating materials were, based upon the dried weight of final coating, is set forth in Table B below.

TABLE B

Composition of Compression Protective Coating

| Component Name | Amount Present (wt. percent based on dried coating) |
|---|---|
| Eudragit NE30D* (30 percent Solid dispersion) | 50.9 percent |
| Eudragit FS30D* (30 percent Solid dispersion) | 33.9 percent |
| Magnesium Stearate | 12.7 percent |
| Sodium Lauryl Sulfate | 2.1 percent |
| Simethicone | 0.4 percent |

Example 2

Preparation of Coated Pharmaceutically Active Agent Granules with Modified Release Coating and Compression Protective Coating Part A: Phenylephrine Layered Particles: Layered phenylephrine granules were first prepared by dissolving 1440 g of phenylephrine hydrochloride and 150 g of Eudragit NE30D™ (500 g of 30 percent aqueous dispersion), for use as a binder, in 1100 g of purified water while mixing at 50 RPM using a laboratory mixer. This mixture was sprayed onto 6560 g of modified starch using the top spray insert of the Glatt GPCG-5/9 fluid bed unit at 40 g/minute and a product temperature of about 35° C. to about 45° C. The final layered particle contained 17.7 percent phenylephrine HCl ("PHE"), 80.5 percent Modified Starch, and 1.8 percent Eudragit NE30D™.

Part B: Preparation of Coated Phenylephrine Granules with Two Coating Layers: 2000 g of phenylephrine layered particles prepared according to Part A above were sequentially and independently coated with Modified Release Coating of Example 1 (at a spray rate of about 30 g/minute) and then Compression Protective Coating of Example 1 (at a spray rate of about 30 g/minute) in a Glatt GPCG-5/9 fluid bed unit with a wurster insert under product temperature conditions of about 20° C. to about 25° C. and an atomization air pressure of 2.0 bar.

The resulting coated PHE granules contained, based upon the total dry weight of the granules and the two coating layers, about 27 percent of the modified release first coating layer (from Modified Release Coating) and about 34 percent of the second coating layer (from Compression Protective Coating). Prior to applying the second coating layer, the resulting coated PHE granules contained, based upon the total dry weight of the granules coating with the first coating layer, about 39 percent of the first coating layer. The finished coated particles were cured in an oven at 50 to 60° C. for 24 hours prior to blending and compression.

Example 3

Production of Tablets for Evaluation containing Phenylephrine with Modified Release Coating and Compression Protective Coating The acetaminophen granulation containing 77.8 percent acetaminophen ("APAP") and shown in Table C below was passed manually through a 30-mesh screen. One kg of blend was created by mixing the coated phenylephrine particles prepared in Example 2, Part B with the acetaminophen granulation.

TABLE C

Components of Tablet

| Ingredients | Percent (w/w) | mg/tab |
|---|---|---|
| Encapsulated Phenylephrine (16.9 percent active) | 34.85 | 344 |
| Acetaminophen Granulation (500 mg) | 65.15 | 643 |
| TOTAL | 100.0 | 987 |

The acetaminophen granulation and coated phenylephrine were combined in the proportions shown in Table C in a V-blender and mixed end-over-end for 5 minutes. The blend was then removed from the blender and compressed on a rotary tablet press at 60 rpm using 2-way tapered, concave modified capsule shape tablet tooling of 0.7 inches (length) by 0.3 inches (width) in order to yield tablets having a weight of 987 mg and a hardness range of about 20 kiloponds.

Example 4

Preparation of Coated Pharmaceutically Active Agent Granules with Only Modified Release Coating Part A: Phenylephrine Layered Particles: Layered phenylephrine granules were first prepared by dissolving 1440 g of phenylephrine hydrochloride and 150 g of Eudragit NE30D™ (500 g of 30 percent aqueous dispersion), for use as a binder, in 1100 g of purified water while mixing at 50 RPM using a laboratory mixer. This mixture was sprayed onto 6560 g of modified starch using the top spray insert of the Glatt GPCG-5/9 at 40 g/minute and a product temperature of about 35° C. to about 45° C. The final layered particle contained 17.7 percent phenylephrine HCl ("PHE"), 80.5 percent Modified Starch, and 1.8 percent Eudragit NE30D™.

Part B: Preparation of Coated Phenylephrine Granules with Only Modified Release Coating Layer: 2000 g of phenylephrine layered particles prepared according to Part A above were independently coated with Modified Release Coating of Example 1 (at a spray rate of about 16 g/minute) in a Glatt GPCG-5/9 fluid bed unit with a wurster insert under product temperature conditions of about 19° C. to about 21° C. and an atomization air pressure of 2.0 bar. The resulting coated PHE granules contained, based upon the total dry weight of the granules and the coating layers, about 35.9 percent by weight of the single coating layer.

Example 5

Production of Tablets for Evaluation Containing Phenylephrine with Modified Release Coating Layer Acetaminophen granulation containing 77.8 percent acetaminophen ("APAP") and shown in Table D below was passed manually through a 30-mesh screen. One kg of blend was created by mixing the coated phenylephrine particle prepared with only 1-layer (in Example 4, Part B)

TABLE D

Components of Tablet

| Ingredients | Percent (w/w) | mg/tab |
|---|---|---|
| Encapsulated Phenylephrine (11.2 percent active) | 20.36 | 179 |
| Acetaminophen Granulation (545 mg) | 79.63 | 700 |
| TOTAL | 100.0 | 879 |

The acetaminophen granulation and coated phenylephrine were combined in the proportions shown in Table D in a V-blender and mixed end-over-end for 5 minutes. The blend was then removed from the blender and compressed on a rotary tablet press at 60 rpm using 2-way tapered, concave modified capsule shape tablet tooling of 0.7 inches (length) by 0.3 inches (width) in order to yield tablets having a weight of 879 mg and a hardness range of about 20 kiloponds.

Example 6

Analysis of Dissolution Data—Phenylephrine Dissolution Test in Different Dissolution Media Part A: DI Water Dissolution Media Analysis: The tablets produced in Example 3 were placed into USP Type II apparatus (Paddles, 50 RPM) containing 900 mL of deionized water at 37° C. A Program VK8000 auto sampler was utilized to remove 10 mL from each vessel at 1, 2, 3, 4, 5, 6, 7, and 8 hours and analyze the pulled samples for PHE by high pressure liquid chromatograph (HPLC).

Part B: Dissolution Analysis: The pulled tablet dissolution samples were analyzed using a Waters XTerra RP18, 3.5 µm, 4.6×50 mm column and a Waters HPLC equipped with a UV detector set at a wavelength of 274 nm, an injection volume of 30 µL, a flow rate of 2.2 mL/minute, and a mobile phase of 0.2 percent formic acid adjusted to pH 3.7 with ammonium hydroxide Phenylephrine coated particles prepared in Examples 2 and 3 were sampled for dissolution in the same manner, except that individual dose of phenylephrine was weighed and sprinkled into each dissolution bath at the beginning of the analysis. The particle samples were analyzed for phenylephrine concentration using a spectrophotometer equipped with UV fiber optic probes set at 274 nm. All tablet and particle samples were analyzed for phenylephrine and APAP quantity in comparison with a standard solution prepared at the theoretical concentration to achieve a 100 percent active release.

The particles of Example 4 containing a only a single Modified Release Coating were compressed into tablets (Example 5) and analyzed for dissolution. The data in Table E demonstrates that the particles of Example 4 provide a modified release of phenylephrine (Column 1). However, this release rate of the phenylephrine is compromised when the particles are compressed into tablets (Column 2), as shown by the lack of sustained release properties even at 60 minutes.

TABLE E

Dissolution Analysis of Phenylephrine tablets and particles in DI water

| Time Point | Column 1<br>Percent Phenylephrine Released in Coated Particles with Single Coating (Example 4) | Column 2<br>Percent Phenylephrine Released in Compressed Tablets containing coated particles (with 1 Coating Layer) at 20 KN (average of 6 vessels); (Example 4) |
|---|---|---|
| 60 min | 15 | 79 |
| 120 min | 26 | 81 |
| 180 min | 36 | 81 |
| 240 min | 45 | 81 |
| 300 min | 52 | 81 |
| 360 min | 58 | 81 |
| 420 min | 64 | 81 |
| 480 min | 68 | 82 |

As shown in Table F, the resulting data also demonstrates that a certain desired modified and sustained release rate is demonstrated with particles having the Modified Release Coating (Column 3). This release rate is further depressed (i.e., slowed) following the addition of the Compression Protective Coating (Column 2). However, after compression into a tablet, the release rate in the compressed tablets (Column 1) is unexpectedly similar to the release rate of particles with the single Modified Release Coating (e.g., compare Column 1 and Column 3), indicating that the second coating unexpectedly acts as a barrier during the tablet compression step in order to retain the desired release rate as demonstrated by the first coating.

TABLE F

Dissolution Analysis of Phenylephrine tablets and particles in DI water

| Time Point | Column 1<br>Percent Phenylephrine Released in Compressed Tablets (Example 3) containing Phenylephrine coated particles (with 2 Coating Layers) at 20 KN (average of 6 Vessels) | Column 2<br>Percent Phenylephrine Released in Coated Particles with 2 Coatings (Example 2, Part A) | Column 3<br>Percent Phenylephrine Released in Coated Particles with Single Coating (Example 2, Part B) |
|---|---|---|---|
| 60 min | 18 | 5.7 | 14.3 |
| 120 min | 34 | 12.3 | 29.7 |
| 180 min | 47 | 20.1 | 42.2 |
| 240 min | 57 | 28.8 | 52.1 |
| 300 min | 65 | 37.9 | 60.3 |
| 360 min | 72 | 46.8 | 67.1 |
| 420 min | 78 | 54.9 | 72.5 |
| 480 min | 83 | 62.0 | 76.9 |
| 720 min | — | 80.1 | 88.3 |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

The invention claimed is:

1. A tablet comprising particles comprising a pharmaceutically active agent, wherein said particles are coated with;
   (a) a first film layer comprising a modified release polymer; and
   (b) a second film layer coating said first film layer, wherein said second film layer comprises (i) a first polymer, wherein said first polymer is a polymer of ethyl acrylate and methyl methacrylate and (ii) a second polymer, wherein said second polymer is a polymer of methyl acrylate, methyl methacrylate and methacrylic acid.

2. A tablet of claim 1, wherein said first polymer is ethyl acrylate, methyl methacrylate copolymer 2:1.

3. A tablet of claim 1, wherein said second polymer is methyl acrylate, methyl methacrylate and methacrylic acid 7:3:1.

4. A tablet of claim 2, wherein said second polymer is methyl acrylate, methyl methacrylate and methacrylic acid 7:3:1.

5. A tablet of claim 1, wherein the weight ratio of said first polymer to said second polymer is from about 1:3 to about 3:1.

6. A tablet of claim 1, wherein the weight ratio of said first polymer to said second polymer is from about 1.5:1 to about 2.5:1.

7. A tablet of claim 1, wherein said second film layer comprises from about 45 percent to about 75 percent, by weight, of said first polymer and from about 20 percent to about 50 percent, by weight, of said second polymer.

8. A tablet of claim 1, wherein the first film layer is from about 10 percent to about 60 percent by weight of the total weight of the particle.

9. A tablet of claim 1, wherein the second film layer is from about 20 percent to about 50 percent by weight of the total weight of the particle.

10. A tablet of claim 1, wherein upon ingestion, said tablet is adapted to release from about 25 to about 40 percent of said pharmaceutically active agent within 2 hours of said ingestion; from about 50 to about 65 percent of said pharmaceutically active agent within 4 hours of said ingestion, and from about 70 to about 80 percent of said pharmaceutically active agent within 6 hours of said ingestion.

11. A particle comprising a pharmaceutically active agent, wherein said particles are coated with;
   (b) a first film layer comprising a modified release polymer; and
   (b) a second film layer coating said first film layer, wherein said second film layer comprises (i) a first polymer, wherein said first polymer is a polymer of ethyl acrylate and methyl methacrylate and (ii) a second polymer, wherein said second polymer is a polymer of methyl acrylate, methyl methacrylate and methacrylic acid.

12. A particle of claim 11, wherein said particle has a particle size of from about 200 microns to about 600 microns.

13. A particle of claim 11, wherein said first polymer is ethyl acrylate, methyl methacrylate copolymer 2:1 and said second polymer is methyl acrylate, methyl methacrylate and methacrylic acid 7:3:1.

14. A particle of claim 11, wherein the weight ratio of said first polymer to said second polymer is from about 1:3 to about 3:1.

15. A particle of claim 11, wherein upon ingestion, said tablet is adapted to release from about 25 to about 40 percent of said pharmaceutically active agent within 2 hours of said ingestion; from about 50 to about 65 percent of said pharmaceutically active agent within 4 hours of said ingestion, and from about 70 to about 80 percent of said pharmaceutically active agent within 6 hours of said ingestion.

16. A method of manufacturing a tablet comprising the steps of i) applying the first film layer to the active particles ii) applying an aqueous dispersion of the first polymer and the second polymer of the second film layer onto the coated particles comprising the first film layer and iii) compressing a plurality of particles of claim 10 to form said tablet.

17. A method of claim 16, wherein said method comprises blending said plurality of particles with a plurality of second particles comprising a second pharmaceutically active agent.

18. A method of claim 16, wherein said particle has a particle size of from about 200 microns to about 600 microns.

19. A method of claim 16, wherein said first polymer is ethyl acrylate, methyl methacrylate copolymer 2:1 and said second polymer is methyl acrylate, methyl methacrylate and methacrylic acid 7:3:1.

20. A method of claim 16, wherein the weight ratio of said first polymer to said second polymer is from about 1:3 to about 3:1.

* * * * *